(12) United States Patent
Kim et al.

(10) Patent No.: US 8,377,272 B2
(45) Date of Patent: *Feb. 19, 2013

(54) ELECTROCHEMICAL BIOSENSOR MEASURING SYSTEM

(75) Inventors: Keun Ki Kim, Seoul (KR); Moon Hwan Kim, Seoul (KR); Jae Hyun Yoo, Seoul (KR); Gang Cui, Seoul (KR); Hakhyun Nam, Seoul (KR); Geun Sig Cha, Seoul (KR)

(73) Assignee: i-SENS, Inc., Seoul (KR)

( * ) Notice: Subject to any disclaimer, the term of this patent is extended or adjusted under 35 U.S.C. 154(b) by 822 days.

This patent is subject to a terminal disclaimer.

(21) Appl. No.: 12/529,008

(22) PCT Filed: Feb. 26, 2008

(86) PCT No.: PCT/KR2008/001105
§ 371 (c)(1),
(2), (4) Date: Aug. 27, 2009

(87) PCT Pub. No.: WO2008/108548
PCT Pub. Date: Sep. 12, 2008

(65) Prior Publication Data
US 2010/0032321 A1 Feb. 11, 2010

(30) Foreign Application Priority Data
Mar. 2, 2007 (KR) .................. 10-2007-0021086

(51) Int. Cl.
*G01N 27/327* (2006.01)
(52) U.S. Cl. ........... 204/403.14; 204/403.01; 205/777.5; 235/462.01; 235/462.04
(58) Field of Classification Search .................. 204/400, 204/403.01–403.05, 403.1–403.13, 403.14; 205/777.5, 778, 792; 600/345–348; 435/4–40.52; 422/68.1, 82.01–82.11, 91, 98; 436/62–71, 436/500–548; 235/462.01, 462.04–462.05, 235/464.41
See application file for complete search history.

(56) References Cited

U.S. PATENT DOCUMENTS

| 3,907,503 A | 9/1975 | Betts et al. |
| 4,714,874 A | 12/1987 | Morris et al. |

(Continued)

FOREIGN PATENT DOCUMENTS

| EP | 1764153 A2 | 3/2007 |
| EP | 1974817 A2 | 10/2008 |

(Continued)

OTHER PUBLICATIONS

JP06112603A—Horimoto et al. (English Equivalent of the Abstract). 1994.*

(Continued)

*Primary Examiner* — Keith Hendricks
*Assistant Examiner* — Susan D Leong
(74) *Attorney, Agent, or Firm* — Klarquist Sparkman, LLP

(57) ABSTRACT

Disclosed is an electrochemical biosensor measuring device which can be used together with an electrochemical biosensor. The biosensor measuring device comprises an electrical connection portion which is electrically connected with the electrodes of the biosensor upon the insertion of the biosensor there into, and a connector having a structure in which at least one light absorption or reflection path sequentially comprising a light emitter-production lot information identification portion-detector unit is provided to identify the production lot information recorded in the biosensor. The electrochemical biosensor measuring device can automatically identify the production lot information of the biosensor, encoded in the form of a hue or hole marks, upon the insertion of the electrochemical biosensor into the measuring device, thereby obviating the need to manually input the production lot information of the biosensor. Thus, inconvenience and the frequency of errors, which occur when a user personally inputs the production lot information, can be reduced, with the result that the measured values can be conveniently and accurately acquired.

28 Claims, 8 Drawing Sheets

U.S. PATENT DOCUMENTS

| | | | |
|---|---|---|---|
| 5,118,369 A * | 6/1992 | Shamir | 156/64 |
| 5,597,532 A | 1/1997 | Connolly | |
| 6,168,957 B1 | 1/2001 | Matzinger et al. | |
| 6,770,487 B2 * | 8/2004 | Crosby | 436/518 |
| 6,814,844 B2 | 11/2004 | Bhullar et al. | |
| 7,111,784 B2 * | 9/2006 | Nakayama | 235/462.04 |
| 2002/0060247 A1 | 5/2002 | Krishnaswamy et al. | |
| 2002/0122746 A1 * | 9/2002 | Yamamori et al. | 422/83 |
| 2005/0089449 A1 | 4/2005 | Polwart et al. | |
| 2005/0279647 A1 | 12/2005 | Beaty | |
| 2006/0042943 A1 * | 3/2006 | Shiraki et al. | 204/403.1 |
| 2006/0144704 A1 | 7/2006 | Ghesquiere et al. | |
| 2006/0175205 A1 * | 8/2006 | Cui et al. | 205/777.5 |

FOREIGN PATENT DOCUMENTS

| | | | |
|---|---|---|---|
| EP | 1688742 A1 | | 4/2009 |
| JP | 04268789 A | * | 9/1992 |
| JP | 06112603 A | * | 4/1994 |
| JP | 2000-171427 A | | 6/2000 |
| JP | 2002-044321 A | | 2/2002 |
| JP | 2004-085827 A | | 3/2004 |
| JP | 2006-134336 A | | 5/2006 |
| JP | 2006-196826 A | | 7/2006 |
| JP | 2006-1898397 | | 7/2006 |
| JP | 2006-234673 A | | 9/2006 |
| KR | 1020040105429 A | | 12/2004 |
| KR | 1020060089464 A | | 8/2006 |
| WO | WO02088739 A1 | | 7/2002 |
| WO | WO03-056345 A | | 7/2003 |
| WO | WO2006-103083 A1 | | 10/2006 |
| WO | WO2007011569 A2 | | 1/2007 |
| WO | WO2009-022779 A1 | | 2/2009 |

OTHER PUBLICATIONS

JP04268789A—Yamada (English Equivalent of the Abstract). 1992.*

International Search Report of the International Searching Authority, mailed May 29, 2008, for corresponding International Application No. PCT/KR2008/001105.

Bauman et al., "Preparation of Immobilized Cholinesterase for Use in Analytical Chemistry," *Analytical Chemistry*, vol. 37, No. 11, pp. 1378-1381, Oct. 1965.

Cassidy et al., "Novel Electrochemical Device for the Detection of Cholesterol or Glucose," *Analyst*, vol. 118, pp. 415-418, Apr. 1993.

K. B. Oldham, "Steady-State Voltammetry" in *Microelectrodes: Theory and Applcations*, Trent University, Peterborough, Canada, Kluwer Academic Publishers, pp. 35-50, 1991.

* cited by examiner

ELECTROCHEMICAL BIOSENSOR MEASURING SYSTEM

CROSS REFERENCE TO RELATED APPLICATIONS

This is the U.S. National Stage of International Application No. PCT/KR2008/001105, filed Feb. 26, 2008, which in turn claims the benefit of and priority to Korean Patent Application No. KR10-2007-0021086, filed Mar. 2, 2007.

TECHNICAL FIELD

The present invention relates to an electrochemical biosensor measuring device.

BACKGROUND ART

For the diagnosis and prophylaxis of diabetes mellitus, the importance of periodically monitoring blood glucose levels is increasingly emphasized. Nowadays, strip-type biosensors designed to be used in hand-held reading devices allow individuals to readily monitor glucose levels in the blood.

Many various commercialized biosensors measure the blood glucose content of blood samples using an electrochemical technique. The principle of the electrochemical technique is based on the following Reaction 1.

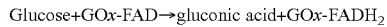

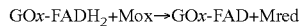 [Reaction 1]

wherein, GOx represents glucose oxidase; GOx-FAD and GOx-FADH$_2$ respectively represent an oxidized and a reduced state of glucose-associated FAD (flavin adenine dinucleotide), a cofactor required for the catalysis of glucose oxidase; and Mox and Mred denote the oxidized and reduced states, respectively, of an electron transfer mediator.

The electrochemical biosensor uses as electron transfer mediators organic electron transfer materials, such as ferrocenes or derivatives thereof, quinines or derivatives thereof, organic or inorganic materials containing transition metals (hexamine ruthenium, polymers containing osmium, potassium ferricyanide and the like), organic conducting salts, and viologens.

The principle by which blood glucose is measured using the biosensor is as follows.

Glucose in the blood is oxidized to gluconic acid by the catalytic activity of glucose oxidase, with the cofactor FAD reduced to FADH$_2$. Then, the reduced cofactor FADH2 transfers electrons to the mediator, so that FADH$_2$ returns to its oxidized state; that is, FAD and the mediator are reduced. The reduced mediator is diffused to the surface of the electrodes. The series of reaction cycles is driven by the anodic potential applied at the working electrode, and redox current proportional to the level of glucose is measured. Compared to biosensors based on colorimetry, electrochemical biosensors (that is, based on electrochemistry) have the advantages of not being influenced by the turbidity or color of the samples and allowing the use of wider range of samples, even cloudy ones, without pretreatment thereof.

Although this electrochemical biosensor is generally convenient when used to monitor and control the amount of blood glucose, its accuracy is greatly dependent on lot-to-lot variation between respective mass-produced lots in which the biosensors are produced. In order to eliminate such variation, most of the commercialized biosensors are designed such that a user directly inputs calibration curve information, which is predetermined at the factory, into a measuring device capable of reading the biosensor. However, this method inconveniences the user a great deal and causes the user to make input errors, thus leading to inaccurate results.

In order to solve this problem, a method by which the resistance of each electrode can be adjusted such that the variations in mass production is corrected (US20060144704A1), a method in which a connection to a resistor bank is made (WO2007011569A2), and a method by which information is read by varying resistance through the adjustment of the length or the thickness of each electrode (US20050279647A1) have been proposed. The methods proposed for the electrochemical biosensors are all based on a technique in which electrical variation is read. Furthermore, a method for distinguishing production lot information by reading the resistivity of a conductor marked on a strip using an electrical method (U.S. Pat. No. 4,714,874) has been proposed.

However, these methods function to accurately adjust resistance, and require a process of mass-producing the sensors first, measuring the statistical characteristics of the sensors, and post-processing the measured information again using a method of adjusting the resistance marked on the sensors. However, the process of accurately adjusting the resistance, marked in large quantities, through the post-processing is very inconvenient, and is difficult to use in practical applications.

Methods in which colored marks are used with a spectral system capable of discriminating colors to realize a colorimetric method (U.S. Pat. No. 3,907,503, U.S. Pat. No. 5,597,532, U.S. Pat. No. 6,168,957), and a method capable of reading bar codes (EP00075223B1, WO02088739A1) have been proposed. These methods using color or bar codes are favorable for a calorimetric method-based sensor using the spectrum system, but they have technical and economic difficulties when applied to a system using an electrochemical measurement mechanism. For example, the size and structure of the area where the electrochemical sensor strip is inserted into the measuring device for the purpose of electrical connection, that is, the connection space of the sensor strip, is very limited when constructing a device and circuit for spectroscopically identifying a structure into which the production lot information is input, which results in a great increase in system construction expense.

Furthermore, instead of the methods of marking the production lot information on the sensor strip, a method of recording information on a container or pack containing a sensor and allowing the information to be read by the measuring device has been proposed. However, this method also has a possibility of causing the user to make an error.

For conventional methods developed in order for users to measure the blood glucose levels thereof using disposable electrochemical biosensor strips without the need to manually input accurate calibration curve information about biosensors, which differs from one production lot to another into a measuring device, the sensors require a long period of time for the preparation thereof, and also require post-processing, in which errors are likely to be made.

Also, conventional devices for reading hue marks using a filter or a monochromator for the wavelength of a light source encounter great spatial limitations and pose problems in the construction of small-sized systems.

Thus, there is a need for a biosensor that has a mark which is simple and can be easily marked within a short time period, such as hue marks, which are convenient to print on a small area of a biosensor, or hole marks, which can be easily prepared simultaneously when the final press process for mass production is performed, thereby allowing the biosensor to be produced on a mass scale. Also, there is a need for a biosensor that has production lot information recorded on the mark through which the production lot information can be thus inputted to an insulation plate of the biosensor, so that when the biosensor is inserted into a measuring device, the production lot information is automatically identified without a mistake being made by a user, thus enabling blood glucose to be conveniently and accurately measured and being economical.

Leading to the present invention, intensive and thorough research into electrochemical biosensors, conducted by the present inventors, aiming to maintain economic efficiency in the construction of the measuring device in which the production lot information thereof can be easily and accurately input into the measuring device and which removes the risk of mistakes being made by the user, thus providing an accurate measurement value, resulted in the finding that, when the production lot information is recorded in the form of hue marks or hole marks on the electrochemical biosensor strip, and when various connectors are connected with a small-sized emitter-detector system to automatically read the production lot information, there is no need for a user to manually input the production lot information of a biosensor, and thus accurate measurement values can be conveniently obtained.

DISCLOSURE OF INVENTION

Technical Problem

Accordingly, the present invention has been made keeping in mind the above problems occurring in the prior art, and an object of the present invention is to provide an electrochemical biosensor measuring device which automatically identifies the production lot information of the biosensor without a mistake being made by a user upon the insertion of an electrochemical biosensor into a measuring device, thus enabling blood glucose to be conveniently and accurately measured.

Technical Solution

In order to accomplish the above object, the present invention provides an electrochemical biosensor measuring device, which measures an electrochemical biosensor composed of plurality of electrodes including at least a working electrode and an auxiliary electrode prepared on at least one or two insulating plates; a capillary sample cell for introducing a sample into the electrodes; a reaction reagent layer, formed on the working electrode, containing a redox enzyme and an electron transfer mediator; an electrical connection portion for connecting the working electrode and the auxiliary electrode; and a production lot information identification portion configured such that production lot information is recorded on at least one insulating plate, which is selected from among at least two planar insulating plates and does not interrupt a connection between the electrodes, wherein the electrochemical biosensor measuring device comprises a connector having a structure in which at least one light absorption or reflection path sequentially comprising a light emitter-production lot information identification portion-detector unit is acquired to thus identify the production lot information recorded in the biosensor.

In the specification, the term "biosensor" is used to have the same meaning as the term "biosensor strip".

Advantageous Effects

The electrochemical biosensor measuring device according to the present invention automatically identifies the production lot information of the biosensor without a mistake being made by a user upon the insertion of an electrochemical biosensor into a measuring device, thus enabling blood glucose to be conveniently and accurately measured.

BRIEF DESCRIPTION OF THE DRAWINGS

The above and other objects, features and advantages of the present invention will be more clearly understood from the following detailed description taken in conjunction with the accompanying drawings, in which.

BRIEF DESCRIPTION OF THE MARK OF DRAWINGS

Figure 1:
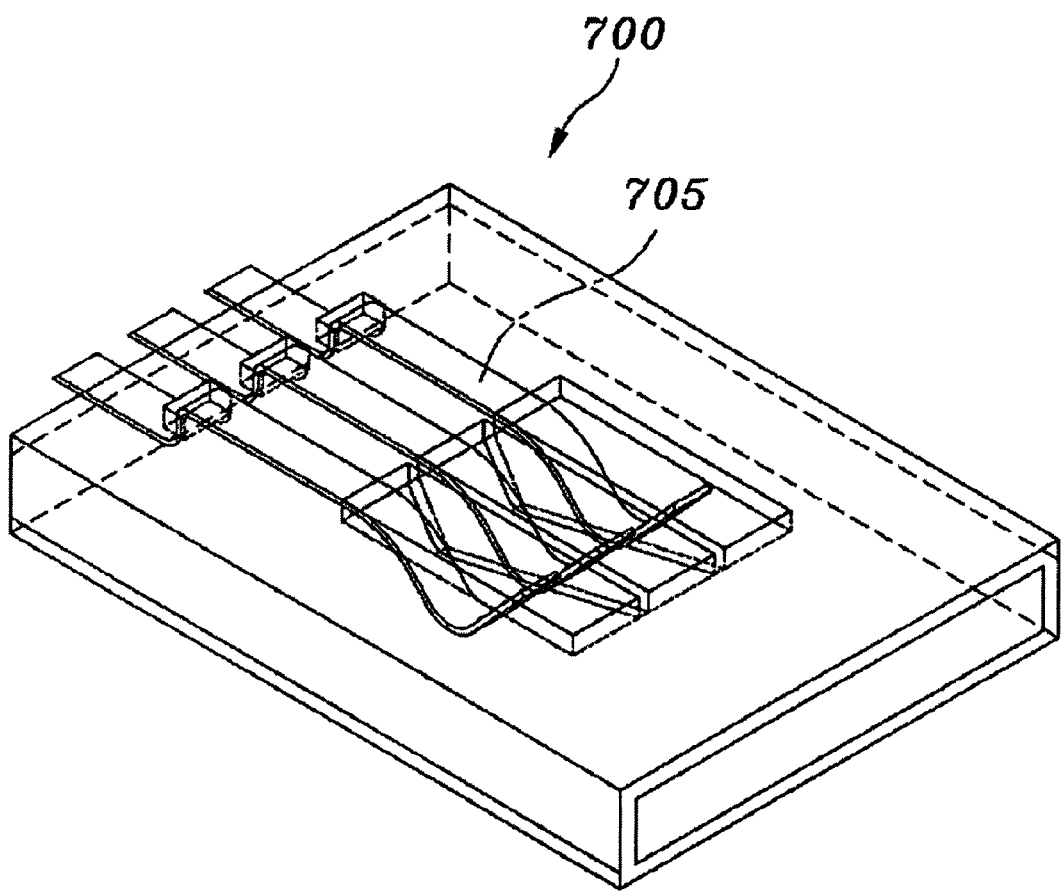
FIG. 1 is a schematic perspective view of a connector having a transparent body installed in a measuring device in accordance with an embodiment of the present invention.

104: electrode
110: biosensor strip
500: production lot information identification portion
700: sensor connector
700a: connector body
700b: sliding structure of connector
702: light emitter
703: detector
704: printed circuit board
705: electrical connection portion
706: transmission window
707: image signal identification device

BEST MODE FOR CARRYING OUT THE INVENTION

The electrodes of the electrochemical biosensor used in the electrochemical biosensor measuring device according to the present invention may be formed on one or both of at least two planar insulating plates. That is, (1) a single working electrode and a single auxiliary electrode (or reference electrode) may be formed on the same planar insulating plate, or (2) may be formed on two planar insulating plates facing each other [parallel electrodes; reference: E. K. Bauman et al., Analytical Chemistry, vol 37, p 1378, 1965; K. B. Oldham in "Microelectrodes: Theory and Applications," Kluwer Academic Publishers, 1991; J. F. Cassidy et al., Analyst, vol 118, p 415].

In addition, the electrodes of the electrochemical biosensor used in the electrochemical biosensor measuring device according to the present invention may further include a sample fluidity determining electrode, which is disposed behind the working electrode and is capable of measuring the fluidity of whole blood samples on a lower planar insulating plate.

The biosensor is described in greater detail taking parallel electrodes as an example.

In the case where the electrochemical biosensor used for the electrochemical biosensor measuring device according to the present invention is constructed using the parallel electrodes, the biosensor may have a structure in which the working electrode and the auxiliary electrode are spaced apart from each other by a pressure-adhesive spacer which is 50-250 μm thick, and are aligned or not aligned with each other and facing each other.

In the thin spacer, a capillary sample cell on the microliter volume scale is provided for injecting a bio-sample in a measurement space defined by the working electrode and the auxiliary electrode and retaining the sample therein. The capillary sample cell includes a sample introducing portion and a micro-path.

In the thin spacer, a sample fluidity determining electrode is placed preferably at a predetermined distance from the working electrode or the auxiliary electrode so that fluorinated blood having a corpuscle volume of 40% can reach the working electrode (or the auxiliary electrode) along a micro-path 0.5-2 mm wide and 50-250 μm high within about 600 ms, and more preferably at a predetermined distance from the working electrode or the auxiliary electrode such that non-fluorinated blood can reach the electrode along the micro-path 0.5-2 mm wide and 50-250 μm high within 300 ms, and still more preferably within 200 ms.

Functioning to introduce a blood sample into one end of the biosensor, the sample-introducing portion is preferably formed in a "L" shape so as to allow the rapid, accurate and convenient introduction of a blood sample from the fore end of the biosensor strip. The sample introducing portion is structured such that an allowance space is formed at the location at which a sample introducing path and an air vent cross each other. By the term "cross", as used herein, it is meant that the sample-introducing path and the air vent are not arranged parallel to each other, but intersect each other at a predetermined point. During measurement, the allowance space helps maintain a constant and accurate volume of the blood sample within the path while discharging the excess sample through the air vent. Also, the allowance space may be used as the place where the sample fluidity determining electrode is disposed. When introduced into the sample introducing portion, a blood sample moves to the electrodes through the micro-path.

In the electrochemical biosensor used in the electrochemical biosensor measuring device according to the present invention, the reaction reagent layer may be formed merely by applying a reagent solution only to the working electrode, or to both the working electrode and the sample fluidity determining electrode. The reaction reagent layer includes an enzyme, such as a glucose oxidase or a lactate oxidase, an electron transfer mediator, a water-soluble polymer, such as a cellulose acetate, a polyvinyl alcohol or a polypyrrol, a fatty acid having 4 to 20 carbon atoms as a reagent for reducing a hematocrit effect, and a hydrophilic quaternary ammonium salt.

In the electrochemical biosensor according to the present invention, electrode connection portions at which the biosensor and the measuring device are electrically connected are designed to exist in the same plane in which the working electrode and auxiliary electrode are connected via connection lines. The level of blood glucose that is measured by the biosensor of the present invention from the results of an electrochemical reaction is provided to the measuring device through the electrode connection portions, and thus can be numerically converted into a precise blood glucose value.

The electrochemical biosensor according to the present invention includes a production lot information identification portion 500 for providing calibration curve information about various concentrations of liquid samples, which is used for respective production lots at the time of manufacturing the biosensor, along with biosensor production lot information, to a user.

The production lot information identification portion 500 may include at least one mark selected from the group consisting of hue marks, hole marks, and light-transmitting film-covered hole marks.

In the electrochemical biosensor measuring device according to the present invention, the production lot information encoded by the hue mark, the hole mark or the light-transmitting film-covered hole mark can be identified using various methods including an optical method, an imaging method, and an IR beam method. The operational principle by which the production lot information identification portion in the measuring device is identified is described in detail below.

In the measuring device, at least two light emitters, for examples, photodiodes, are integrated within a small space. Photodiodes useful in the present invention are preferably three-component light emitting diodes emitting red, blue and green colors, or four-component light emitting diodes emitting white, red, blue and blue colors, but are not limited thereto. The light emitter may use an infrared light source. Using the light emitted from the photodiodes or the infrared light source, the information encoded by the hue mark, the hole mark or the light-transmitting film-covered hole mark marked in the production lot information identification portion of the biosensor is detected.

The hue mark may display the information about differences between production lots according to differences in color, brightness, or chroma. The hole mark may encode the information about differences between production lots as a combination of close and open holes. As for the light-transmitting film-covered hole mark, its information about differences between production lots can be indicated by varying the degree of transmission of the film covering the hole mark. It is preferred that the number of hue marks or hole marks be adjusted to fall within the range of 1 to 10.

The light sensed by the production lot information identification portion is transmitted therethrough or reflected therefrom, and experiences a change in intensity or wavelength. The transmitted or reflected light is detected by a detector 703, such as an optical identifier, placed at a location between the light emitters 702. The change in the intensity and wavelength of light, as detected by the detector 703, is delivered to a calculation system (not shown) from which the change appears as the production lot information of the biosensor.

The light emitter 702 and the detector 703 may be constructed in a separated or integrated structure. The detector 703 may be located in the same plane as the light emitter 702 when it is adapted to detect the light reflected from the hue marks, the hole marks or the light-transmitting film-covered hole marks, and may be located in a plane opposite the light emitter 702 when it is adapted to detect the transmitted light.

With regard to the hue marks, the differences in the image made by their combinations correspond to differences in the information about production lots. The images of the marks are detected by an image signal identification device 707, such as a CCD camera, and are transmitted to a calculation system (not shown) from which the image signal appears as the production lot information of the biosensor.

The production lot information identification portion 500, adapted for the electrochemical biosensor, which is used for the electrochemical biosensor measuring device according to the present invention, is not limited to a parallel type electrochemical biosensor, and may also be applied to a plane type electrochemical biosensor, which is implemented such that the working electrode and the auxiliary electrode are formed in the same plate and are thus operated, and to a differential type electrochemical biosensor, which is implemented such that the parallel type electrochemical biosensor and the plane type electrochemical biosensor process signals differently.

A connector used in the electrochemical biosensor measuring device according to the present invention preferably has a structure in which one or more absorption or reflection path(s) comprising a light emitter-production lot information identification portion-detector can be realized, thereby identifying the production lot information marked on the biosensor.

As shown in FIG. 1, the connector 700, for example, may be formed of a body made of transparent material, such as transparent acrylic or plastic.

Figure 2:
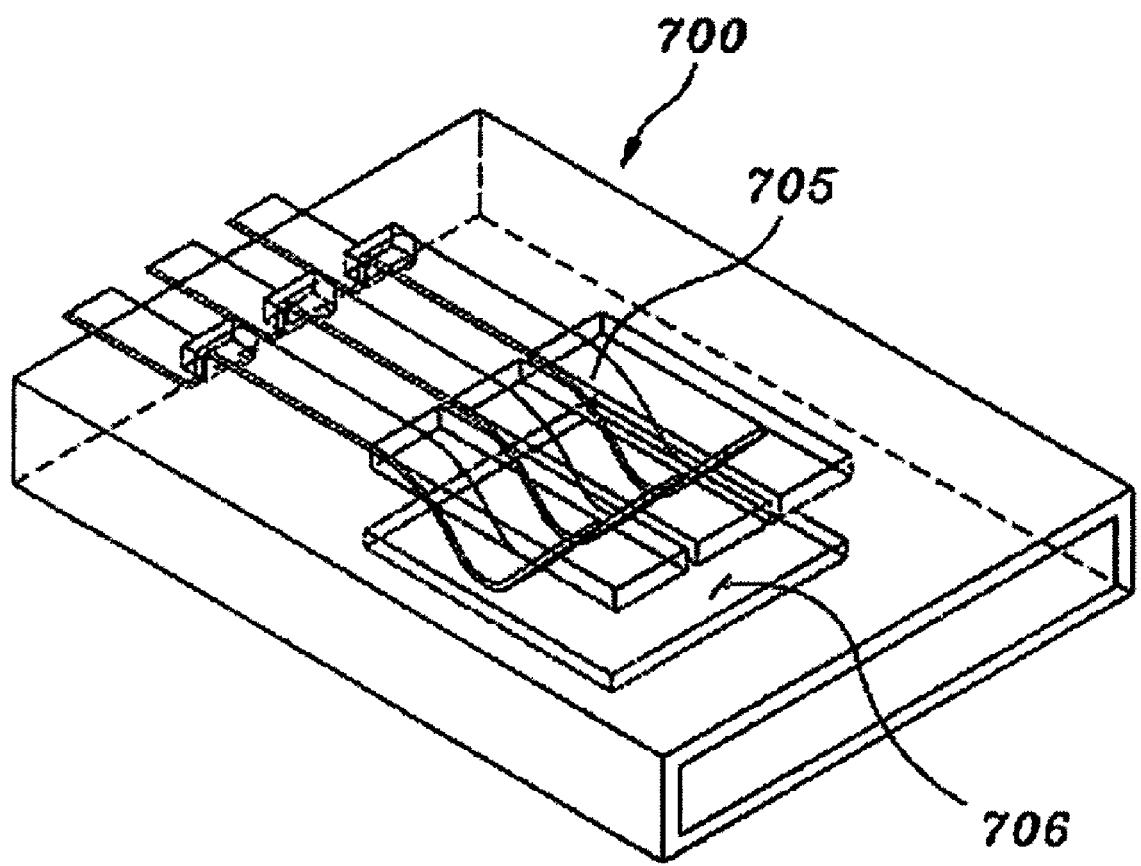
FIG. 2 is a schematic perspective view of a connector provided with a transmission window in one side thereof, which is used in a measuring device in accordance with an embodiment of the present invention.
Figure 3:
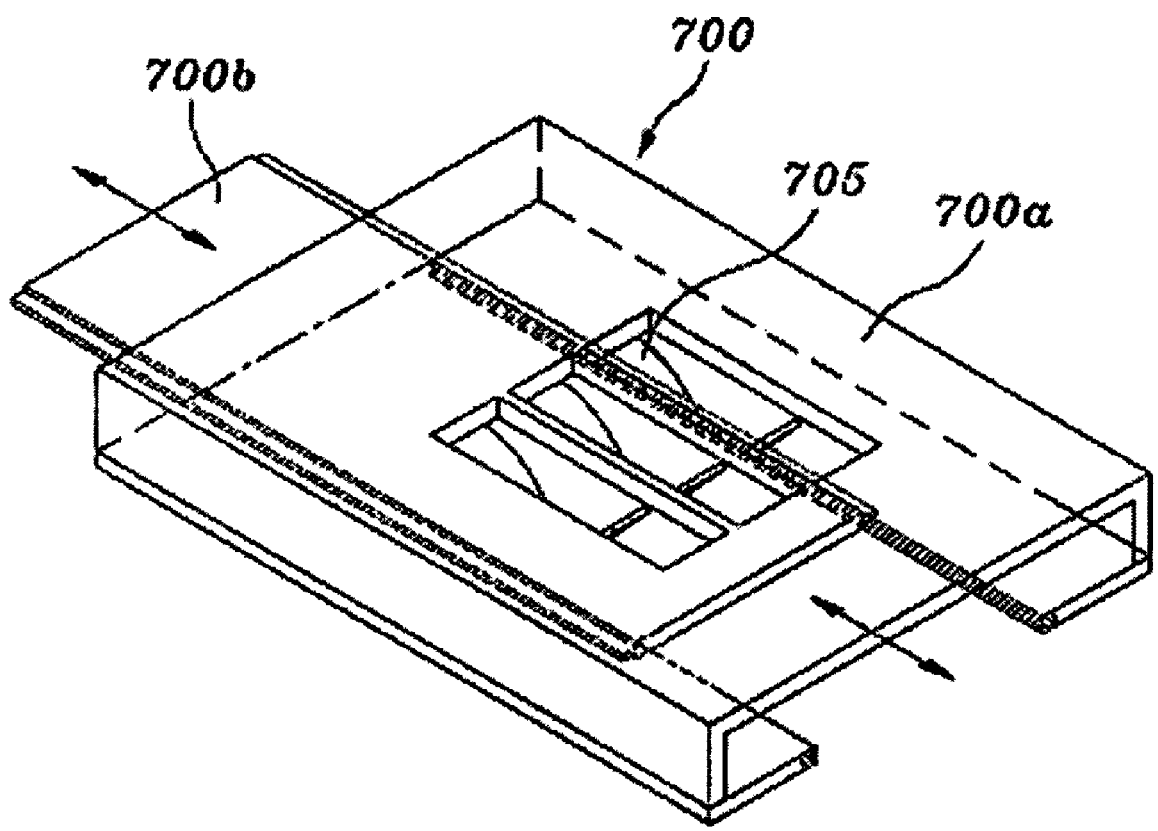
FIG. 3 is a schematic perspective view of a connector constructed to have a sliding structure, which is used in a measuring device in accordance with an embodiment of the present invention.

Furthermore, the connector 700, as shown in FIG. 2, may be provided with a transmission window 706 in one side thereof so that infrared rays absorbed or reflected via the light emitter-production lot information identification portion-detector 700 are passed therethrough. Accordingly, even when the connector is made of opaque material, or even when the body of the connector is colored, the light beams radiated by the light emitters 702 can easily reach the production lot information identification portion of the biosensor through the transmission window 706, and thus the production lot information can be identified.

Furthermore, in order to pass the light beams, which are absorbed or reflected via the light emitter-production lot information identification portion-detector, through the connector 700, the connector 700 may be manufactured such that one side thereof has a sliding door structure 700*b*. In greater detail, when a biosensor is inserted into the connector, the sliding door structure 700*b* of the connector is pushed along with the biosensor in the insertion direction of the biosensor, thus realizing the path along which the light beams can reach the production lot information identification portion of the biosensor. In this case, the sliding door structure 700*b* may be connected to a device that can passively or automatically remove the biosensor, and thus the biosensor can be easily separated and removed from the biosensor measuring device using the removing device (not shown) after the use of the biosensor.

Figure 4:
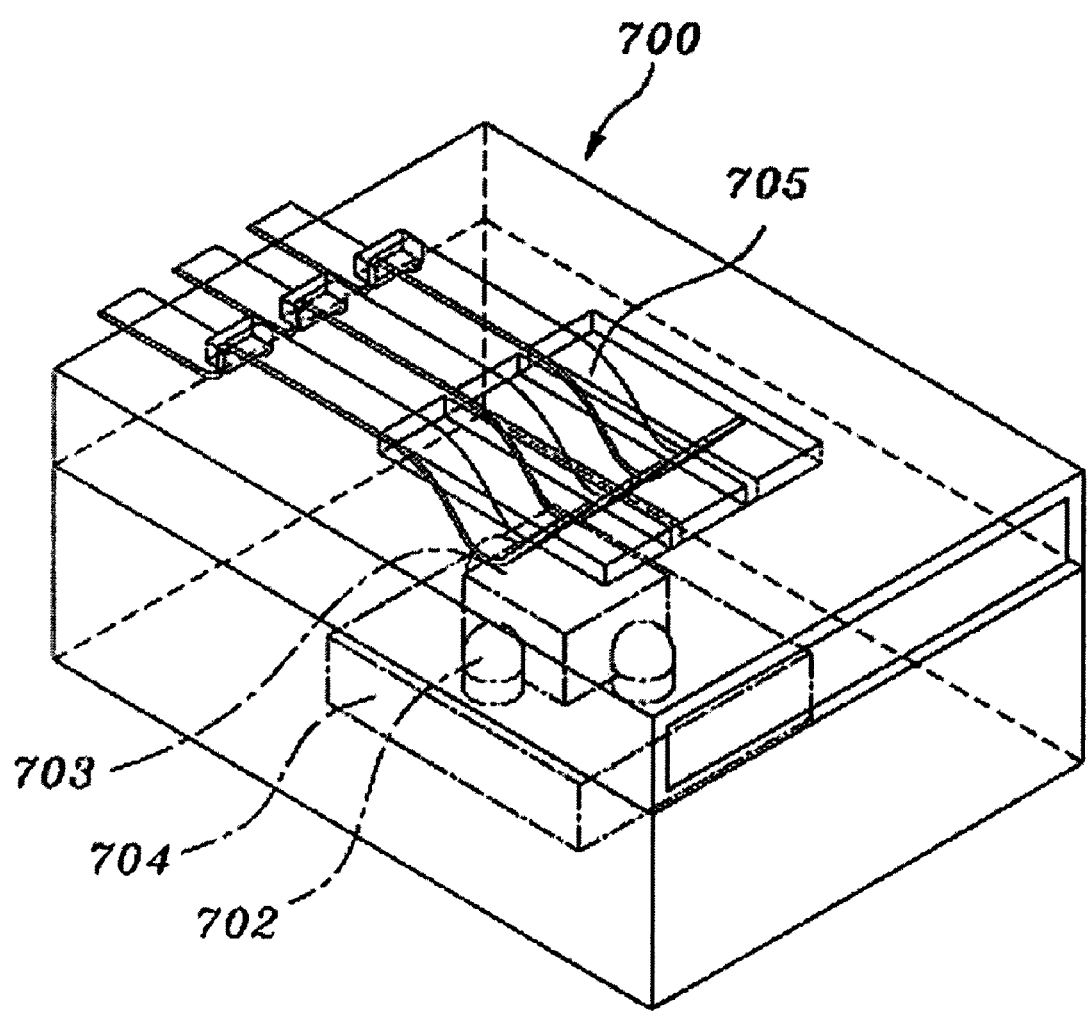
FIG. 4 is a schematic perspective view of a connector comprising a light emitter, a detector and an electrical connection portion in an integrated structure therein, which is used in a measuring device in accordance with an embodiment of the present invention.
Figure 5:
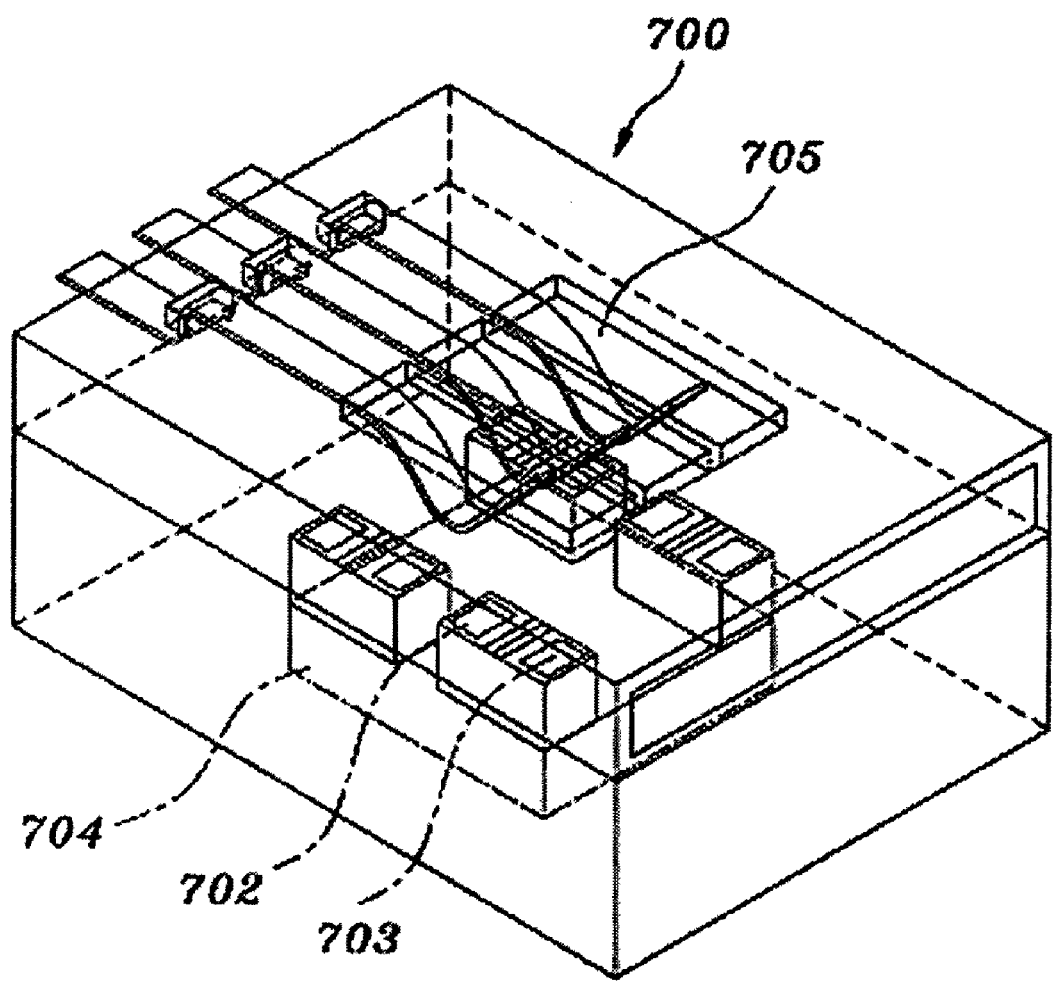
FIG. 5 is a schematic perspective view of a connector comprising a light emitter, a detector system and an electrical connection portion in an integrated structure therein, which is used in a measuring device in accordance with an embodiment of the present invention.
Figure 6:
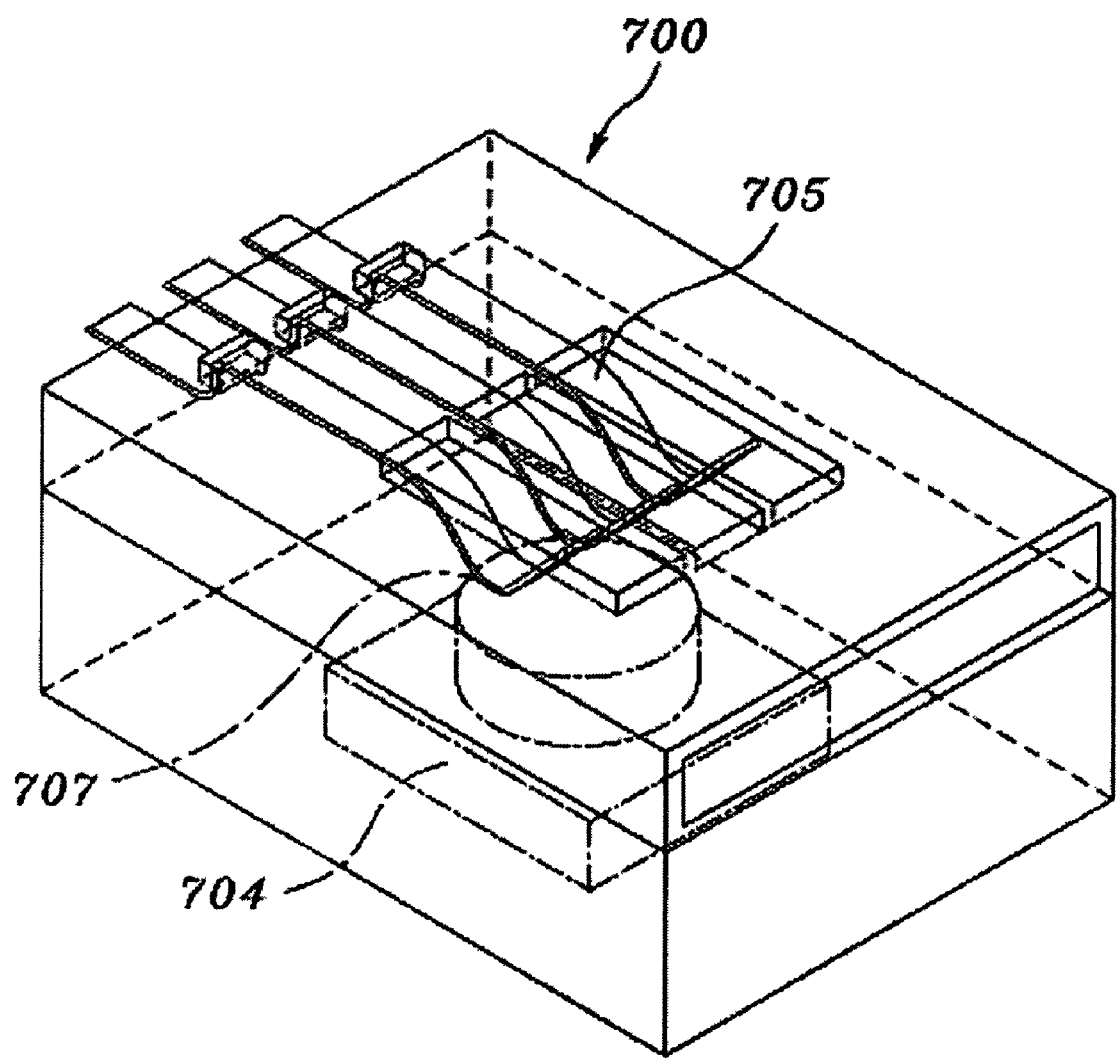
FIG. 6 is a schematic perspective view of a connector comprising an image signal identification device and an electrical connection portion in an integrated structure, which is used in a measuring device in accordance with an embodiment of the present invention.

As shown in FIGS. 4 to 6, the connector may comprise the light emitters 702, the detector 703 and electrical connection portions 705 in an integrated structure within the body thereof. For example, the connector of FIG. 4 employs a three-color diode as a light emitter 702 and an optical identifier as a detector in an integrate structure, by which differences in the color, brightness or chroma of the production lot information identification portion of the biosensor are detected to thus identify the production lot information. The connector of FIG. 5 employs an infrared light source 703 as a light emitter 702 and an optical identifier as a detector 703 in an integrated structure in order to discriminate the differences in the color, brightness or chroma of the production lot information identification portion of the biosensor, thereby identifying production lot information. FIG. 6 shows a connector 700 which employs an image signal identification device 707 as a detector by which the image encoded by the hue mark of the production lot information identification portion is detected so as to identify the production lot information. Preferably, the image signal identification device may be a charge coupled device (CCD) camera.

It may be generally difficult or uneconomical to construct a system in which a hue or hole mark identification circuit of a photospectrometer system is installed in combination with a circuit and device for measuring the biosensor of an electrochemical system. With the recent development of small-sized light emitting device, detecting device and circuit design technologies, however, a system, the constitution of which was considered unfeasible in the past due to incompatibility between constitutional components, can be easily and economically implemented in a small circuit space at minimal cost.

Conventional devices for reading hue marks using a filter or a monochromator to determine the wavelength of a light source encounter great spatial limitations and pose problems in the construction of small-sized systems. In the recognition of production lot information, in contrast, the biosensor according to the present invention can readily identify hue marks and allows the construction of an economical system because it uses small-sized three-component light emitting diodes emitting red, blue and green colors at the same time and detects overall variation in the light reflected from or transmitted through the hue marks with a small-sized optical identification device. The advantage of such electrochemical measurement is combined with the advantages of recent small-sized spectral device technologies obtained by the development of technology, and thus a biosensor that is economical and provides precise measurement values can be provided.

Furthermore, the present invention provides a measuring method using the electrochemical biosensor measuring device, comprising:

inserting a biosensor provided with a production lot identification portion containing production lot information into the connector port of the biosensor measuring device to activate its power (step 1);

identifying the production lot information of the biosensor inserted at Step 1 (step 2);

activating measurement and operation processes of the biosensor measuring device in conformity with the production lot information identified at Step 2 (step 3); and introducing a liquid sample to the sample inlet of the biosensor to result in quantitative electrochemical information about the sample, quantifying a specific component of the liquid sample, and displaying quantification results (step 4).

The measuring method using the biosensor measuring device of the present invention is described stepwise in detail below.

In step 1, a biosensor provided with a production lot identification portion containing production lot information into the connector port of the biosensor measuring device is inserted to activate its power.

Figure 7:
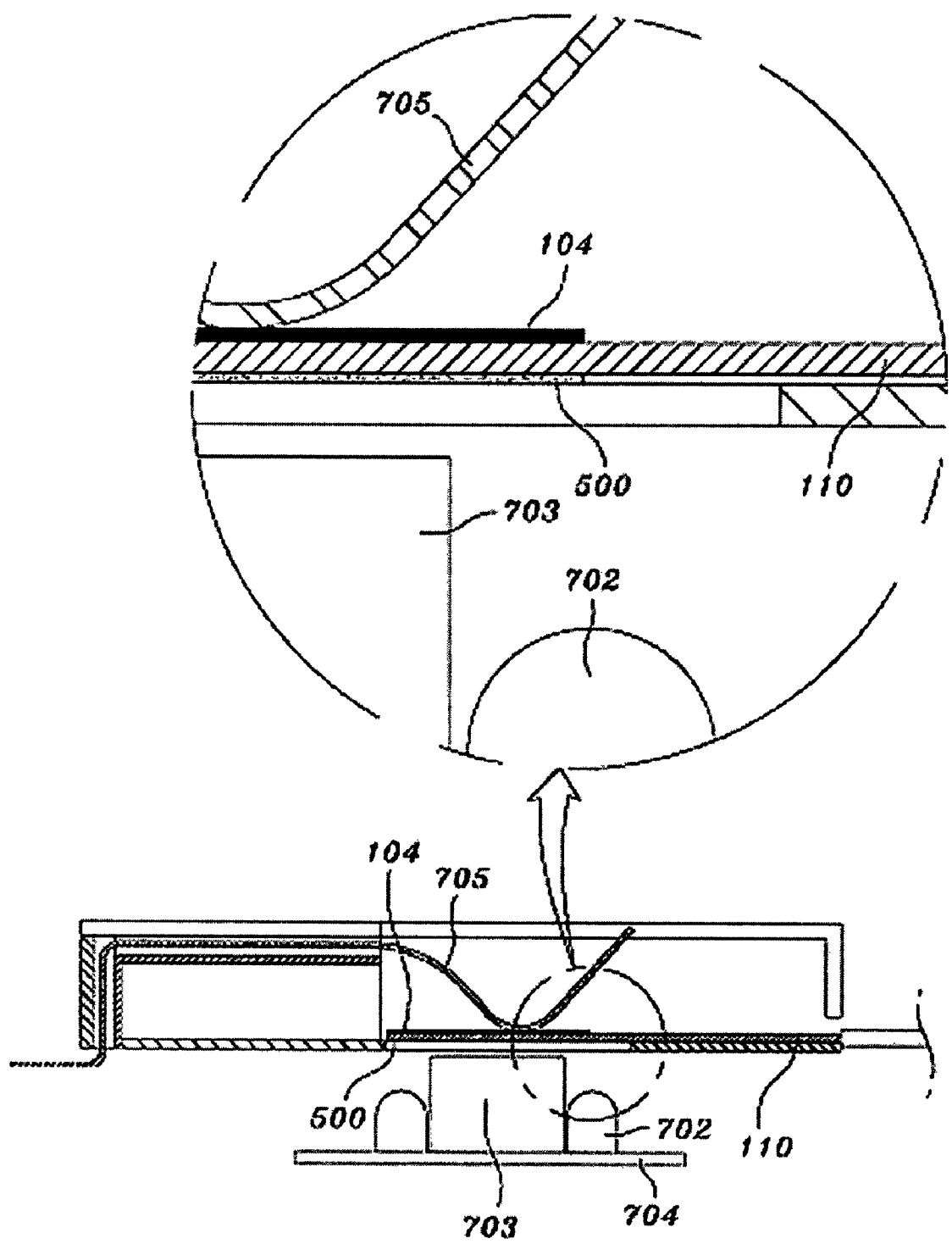
FIG. 7 is a schematic sectional view showing the insertion of a biosensor to a connector in a measuring device according to an embodiment of the present invention.
Figure 8:
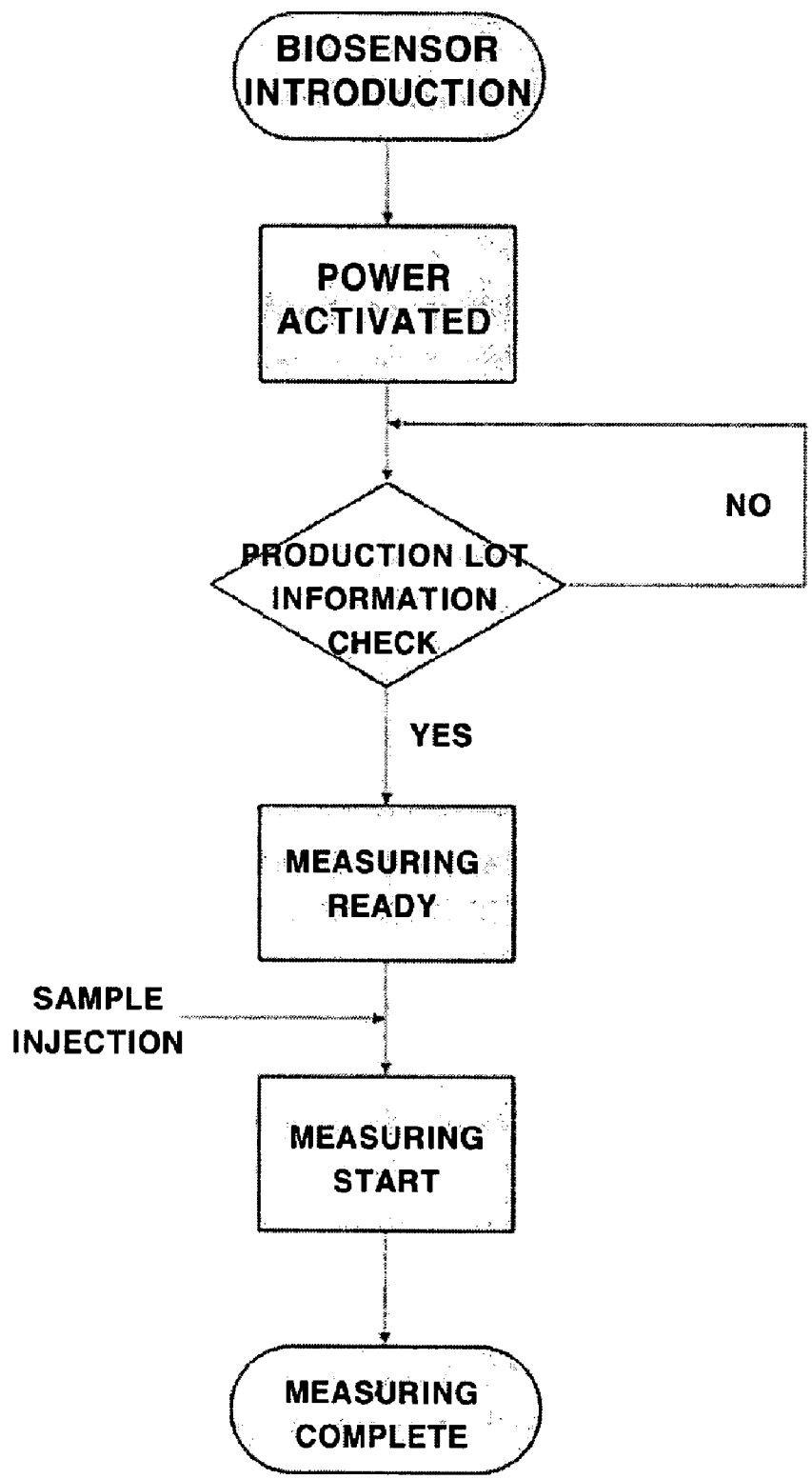
FIG. 8 is a flow chart showing a measuring process using a biosensor measuring device in accordance with the present invention.

As shown in FIG. 7, the biosensor is inserted into the connector 700 of the measuring device through a sensor injection hole. Upon insertion, the electrodes 104 of the biosensor 110 are electrically connected to the electrical connection portions 705 of the connector to allow electric current to flow, therefore operating the measuring device.

Next, Step 2 serves to identify the production lot information of the biosensor which is inserted at step 1.

As shown in FIG. 7, the insertion of the biosensor 110 into the connector 700 electrically connects the biosensor to the measuring device through the connector 700 to activate the light emitter 702-detector 703 system in the measuring device, thereby identifying the production lot information of the biosensor using the activated light emitter 702-detector 703 system.

In this regard, the identification of the production lot information is implemented by the recognition of at least one mark selected from the group comprising a hue mark, a hole mark and a light-transmitting film-covered hole mark.

The hue mark may display the information about differences between production lots by differences in the color, brightness, or chroma of a plurality of color images. The hole mark may encode the information about differences between production lots in the form of a combination of holes which are independently open or closed. As for the light-transmitting film-covered hole mark, its information about differences between production lots can be displayed by varying the degree of transmission of films covering open holes. It is preferred that the number of hue marks or hole marks be adjusted to fall within the range of 1 to 10.

The identification of the production lot information can be achieved as follows.

For instance, light beams are emitted sequentially from three-component photodiodes of red, green and blue colors or four-component photodiodes of white, red, green and blue colors to detect the hue marks, hole marks or light-transmitting film-covered hole marks of the production lot information identification portion. Variations in wavelength, color, brightness and chroma depending on the degrees of reflection or transmission of detected light beams are detected by an optical identification device, so that the production lot information of the biosensor can be identified.

In another example, image signals are detected from the hue marks of the production lot information identification portion, thereby identifying the production lot information of the biosensor.

In Step 3, measurement and operation processes of the biosensor measuring device are activated in conformity with the production lot information identified at Step 2.

Following the identification of the production lot information at Step 2, in greater detail, the measuring device has measurement and operation processes activated in conformity with the identified production lot information, and enters a standby state for sample measurement.

Finally, Step 4 serves to introduce a liquid sample to the sample inlet of the biosensor to result in quantitative electrochemical information about the sample, quantify a specific component of the liquid sample, and display the quantified results.

In greater detail, the introduction of a liquid sample into the biosensor strip inserted into the measuring device (step a) creates a predetermined potential difference between the working electrode and the auxiliary electrode and between the sample fluidity determining electrode and the auxiliary electrode (step b), the sample flowing into the sample introducing portion of the strip causes primary electrical variation between the working electrode and the auxiliary electrode to adjust the voltages between the electrodes to the same value (step c). The sample fluidity determining electrode senses the flow of the sample to cause secondary electrical variation, and the voltage between the auxiliary electrode and the sample fluidity determining electrode is adjusted to be the same, thus providing information about the time difference with the electrical variation primarily sensed by the working electrode (step d). When a liquid sample is sufficiently mixed with a reagent applied to the working electrode, voltage is applied again between the working electrode and the auxiliary electrode to cause a cyclic reaction in a parallel-type thin layer electrochemical cell, and the stationary current value thus reached is read (step e). The amount of the substrate present in the sample is analyzed using the time information obtained in step d and the stationary current value obtained in step e to determine the level of a specific component, such as blood glucose, and the result is displayed in a window.

As described hitherto, the electrochemical biosensor measuring device according to the present invention automatically identifies the production lot information of the biosensor without a mistake being made by a user upon the insertion of an electrochemical biosensor into a measuring device, thus enabling blood glucose to be conveniently and accurately measured.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. An electrochemical biosensor measuring device, which measures an electrochemical biosensor composed of plurality of electrodes including at least a working electrode and an auxiliary electrode prepared on at least one or two insulating plates; a capillary sample cell for introducing a sample into the electrodes; a reaction reagent layer, formed on the working electrode, containing a redox enzyme and an electron transfer mediator; an electrical connection portion for connecting the working electrode and the auxiliary electrode; and a production lot information identification portion configured such that production lot information is recorded on at least one insulating plate, and does not interrupt a connection between the electrodes, wherein the biosensor measuring device comprises a light emitter, a detector and a connector having a structure in which at least one light absorption or reflection path sequentially through a light emitter-production lot information identification portion-detector is provided to identify the production lot information recorded in the biosensor, and wherein the connector is provided with a transmission window in one side thereof so that the light beams absorbed or reflected via the light emitter-production lot information identification portion-detector pass through the connector;

wherein the connector further includes a sliding door structure that covers a portion of the transmission window, wherein the sliding door structure provides a path through which the light beam can reach the production lot information identification portion.

2. The electrochemical biosensor measuring device according to claim 1, wherein the plurality of electrodes further include a sample fluidity determining electrode.

3. The electrochemical biosensor measuring device according to claim 1, wherein the production lot information identification portion includes at least one mark selected from a group consisting of a hue mark, a hole mark and a light-transmitting film-covered hole mark.

4. The electrochemical biosensor measuring device according to claim 3, wherein the production lot information identification portion includes one or more hue mark(s) displaying the information about differences between production lots by differences in the color, brightness, or chroma of one or more color image(s).

5. The electrochemical biosensor measuring device according to claim 3, wherein the production lot information identification portion includes one or more hole mark(s) displaying the information about differences between production lots by differences in the combination of one or more hole mark(s), each hole mark being an open or closed hole.

6. The electrochemical biosensor measuring device according to claim 3, wherein the production lot information identification portion includes one or more light-transmitting film covered hole mark(s) displaying the information about differences between production lots by differences in the degree of transmission of light through the light-transmitting film of the one or more light-transmitting film covered hole mark(s).

7. The electrochemical biosensor measuring device according to claim 4, wherein the number of the hue marks ranges from 1 to 10.

8. The electrochemical biosensor measuring device according to claim 1, wherein the light emitter is composed of three-component photodiodes that emit red, green and blue colors or four-components photodiodes that emit white, red, green and blue colors.

9. The electrochemical biosensor measuring device according to claim 1, wherein the light emitter is an infrared light source.

10. The electrochemical biosensor measuring device according to claim 1, wherein the production lot information identification portion detector is an optical identification device which identifies the production lot information by discerning differences in the color, brightness or chroma of the hue marks, hole marks or light-transmitting film-covered hole marks of the production lot information identification portion.

11. The electrochemical biosensor measuring device according to claim 4, wherein the production lot information identification portion detector is an image signal identification device which identifies the production lot information by discerning differences in the image signal of the hue mark of the production lot information identification portion.

12. The electrochemical biosensor measuring device according to claim 1, wherein the light emitter and the detector are constructed in a separate or integrated structure.

13. The electrochemical biosensor measuring device according to claim 1, wherein the connector has a body made of a transparent material.

14. The electrochemical biosensor measuring device according to claim 1, wherein the sliding door structure is connected to a device that can passively or automatically remove the biosensor.

15. The electrochemical biosensor measuring device according to claim 1, wherein the connector includes a body made of a transparent material and an electrical connection portion; and the light emitter, the detector and the electrical connection portion are present in an integrated structure within the body.

16. A measuring method using a biosensor measuring device, comprising:
inserting the electrochemical biosensor as recited in claim 1 into the connector port of the measuring device according to claim 1 to activate its power (step 1);
identifying the production lot information of the biosensor inserted at Step 1 (step 2);
activating the measurement and operation processes of the biosensor measuring device in conformity with the production lot information identified at Step 2 (step 3); and
introducing a liquid sample to the sample inlet of the biosensor to result in quantitative electrochemical information about the sample, quantifying a specific component of the liquid sample, and displaying quantification results (step 4).

17. The measuring method according to claim 16, wherein the identifying step is carried out by detecting at least one mark selected from a group consisting of a hue mark, a hole mark and a light-transmitting film-covered hole mark.

18. The measuring method according to claim 17, wherein the hue mark displays information about differences between production lots by differences in the color, brightness, or chroma of a plurality of color images.

19. The measuring method according to claim 17, wherein the hole mark displays information about differences between production lots by differences in the combination of a plurality of holes which are independently open or closed.

20. The measuring method according to claim 17, wherein the light-transmitting-covered hole mark displays information about differences between production lots by differences in the degree of transmission of light through a plurality of light-transmitting films covering corresponding open holes.

21. The measuring method according to claim 18, wherein the number of the hue marks ranges from 1 to 10.

22. The measuring method according to claim 16, wherein the identifying the production lot information step is carried out by applying light from three-component photodiodes that emit red, green and blue colors or four-components photodiodes that emit white, red, green and blue colors to a hue mark, a hole mark or a light-transmitting film-covered hole mark of a production lot information identification portion, and detecting a variation or difference in the wavelength, color, brightness or chroma of the light according to reflection from or transmission through the mark using an optical identification device.

23. The measuring method according to claim 16, wherein the identifying the production lot information step is carried out by applying light from one or more infrared light sources capable of emitting infrared light to a hue mark, a hole mark or a light-transmitting film-covered hole mark of a production lot information identification portion, and detecting a variation or difference in the wavelength, color, brightness or chroma of the light according to the reflection from or the transmission through the mark using one or more optical identification devices.

24. The measuring method according to claim 16, wherein the identifying the production lot information step is carried out by detecting an image signal from a hue mark of a production lot information identification portion with an image signal identification device and analyzing the information encoded by the image signal.

25. The electrochemical biosensor measuring device according to claim 5, wherein the number of the hole marks ranges from 1 to 10.

26. The electrochemical biosensor measuring device according to claim 6, wherein the number of the hole marks ranges from 1 to 10.

27. The measuring method according to claim 19, wherein the number of the hole marks ranges from 1 to 10.

28. The measuring method according to claim 20, wherein the number of the hole marks ranges from 1 to 10.

* * * * *